(12) United States Patent
Shomali et al.

(10) Patent No.: US 10,398,796 B2
(45) Date of Patent: Sep. 3, 2019

(54) GAS GENERATION MODULE

(71) Applicants: Eniware, LLC., Bethesda, MD (US); Noxilizer, Inc., Baltimore, MD (US)

(72) Inventors: Majdi F. Shomali, Arlington, VA (US); James E. Bernstein, Washington, DC (US); David B. Opie, Severna Park, MD (US); Alind Sahay, West Chester, PA (US); Jeffrey C. Soreide, Baltimore, MD (US)

(73) Assignees: ENIWARE, LLC, Washington, DC (US); NOXILIZER, INC., Baltimore, MD (US)

( * ) Notice: Subject to any disclaimer, the term of this patent is extended or adjusted under 35 U.S.C. 154(b) by 294 days.

(21) Appl. No.: 15/214,025

(22) Filed: Jul. 19, 2016

(65) Prior Publication Data

US 2018/0021466 A1 Jan. 25, 2018

(51) Int. Cl.
*A61L 2/20* (2006.01)
*A01N 59/00* (2006.01)
(Continued)

(52) U.S. Cl.
CPC ............... *A61L 2/20* (2013.01); *A01N 25/34* (2013.01); *A01N 59/00* (2013.01); *A61L 9/046* (2013.01); *A61L 9/12* (2013.01); *C01B 21/36* (2013.01); *A61L 9/145* (2013.01); *A61L 2202/11* (2013.01); *A61L 2202/13* (2013.01); *A61L 2202/16* (2013.01); *A61L 2202/25* (2013.01); *A61L 2209/14* (2013.01)

(58) Field of Classification Search
CPC ............ A61L 2/20; A01N 25/34; A01N 59/00
See application file for complete search history.

(56) References Cited

U.S. PATENT DOCUMENTS 5,302,358 A 4/1994 Andersen et al.
6,663,902 B1 * 12/2003 Hei ..................... A01N 59/00
424/661
(Continued)

FOREIGN PATENT DOCUMENTS

CN 201955978 U 8/2011
WO 2011/011189 A1 1/2011

OTHER PUBLICATIONS

International Search Report PCT/US2017/042131 dated Dec. 4, 2017.
(Continued)

*Primary Examiner* — Jill A Warden
(74) *Attorney, Agent, or Firm* — Pillsbury Winthrop Shaw Pittman LLP (57) ABSTRACT

A sterilant source for use in a portable sterilant system includes a gas-impermeable vial, a frangible ampule containing a first sterilant gas precursor material, disposed within the gas-impermeable vial, a second sterilant gas precursor material, disposed within the gas-impermeable vial and outside the ampule. The first and second sterilant gas precursor materials are selected to be mutually reactive to generate a sterilant gas. The system further includes an activation mechanism, actuatable to break the frangible ampule to release the first sterilant gas precursor material to allow it to react with the second sterilant gas precursor material to generate the sterilant gas.

10 Claims, 6 Drawing Sheets

(51) Int. Cl.
    *C01B 21/36*     (2006.01)
    *A01N 25/34*     (2006.01)
    *A61L 9/04*     (2006.01)
    *A61L 9/12*     (2006.01)
    *A61L 9/14*     (2006.01)

(56) References Cited

U.S. PATENT DOCUMENTS

| | | |
|---|---|---|
| 8,017,074 B2 | 9/2011 | Arnold et al. |
| 8,101,589 B2 | 1/2012 | Arnold et al. |
| 8,425,837 B2 | 4/2013 | Carbone et al. |
| 8,703,066 B2 | 4/2014 | Arnold et al. |
| 8,721,984 B2 | 5/2014 | Carbone et al. |
| 8,808,622 B2 | 8/2014 | Arnold et al. |
| 9,180,217 B2 | 11/2015 | Arnold et al. |
| 2006/0127273 A1 | 6/2006 | Kampa |
| 2012/0164056 A1* | 6/2012 | Haddad .................... A61L 2/20 423/400 |
| 2013/0217107 A1 | 8/2013 | Pederson et al. |

OTHER PUBLICATIONS

Written Opinion of the International Searching Authority PCT/US2017/042131 dated Dec. 4, 2017.

\* cited by examiner

GAS GENERATION MODULE

BACKGROUND OF THE INVENTION

1. Field

This application relates generally to devices for generating gases and more particularly to a gas generating device that may be used with a portable sterilization system.

2. Description of Related Art

Laboratory, factory, and hospital environment sterilization can be achieved using a variety of devices that tend to require connection to relatively large, static sources of energy or sterilizing materials such as fluids or gases. Field sterilization may find uses in remote locations where such connections are unavailable, inconvenient, or excessively expensive to put into place. Portable sterilizers have been developed to meet these needs.

Such portable sterilizing systems still require a source of sterilant gas, which preferably is itself portable, durable, and operable without consumption of large amounts of energy.

BRIEF SUMMARY OF THE INVENTION

A sterilant source for use in a portable sterilant system includes a gas-impermeable vial, a frangible ampule containing a first sterilant gas precursor material, disposed within the gas-impermeable vial, a second sterilant gas precursor material, disposed within the gas-impermeable vial and outside the ampule, the first and second sterilant gas precursor materials being selected to be mutually reactive to generate a sterilant gas, and an activation mechanism, configured and arranged to be actuatable to break the frangible ampule to release the first sterilant gas precursor material to allow it to react with the second sterilant gas precursor material to generate the sterilant gas.

A sterilizing system includes a sealable gas-impermeable sterilizing chamber, and a port, configured and arranged to receive a sterilant gas generating module, and to allow a sterilant gas generated by the sterilant gas generating module to flow into the sterilizing chamber, and to prevent the sterilant gas from escaping the sterilizing chamber.

A method of producing a sterilant gas in a portable sterilant system includes using a sterilant source or sterilizing system as in the foregoing paragraphs.

DETAILED DESCRIPTION OF THE INVENTION

Figure 1:
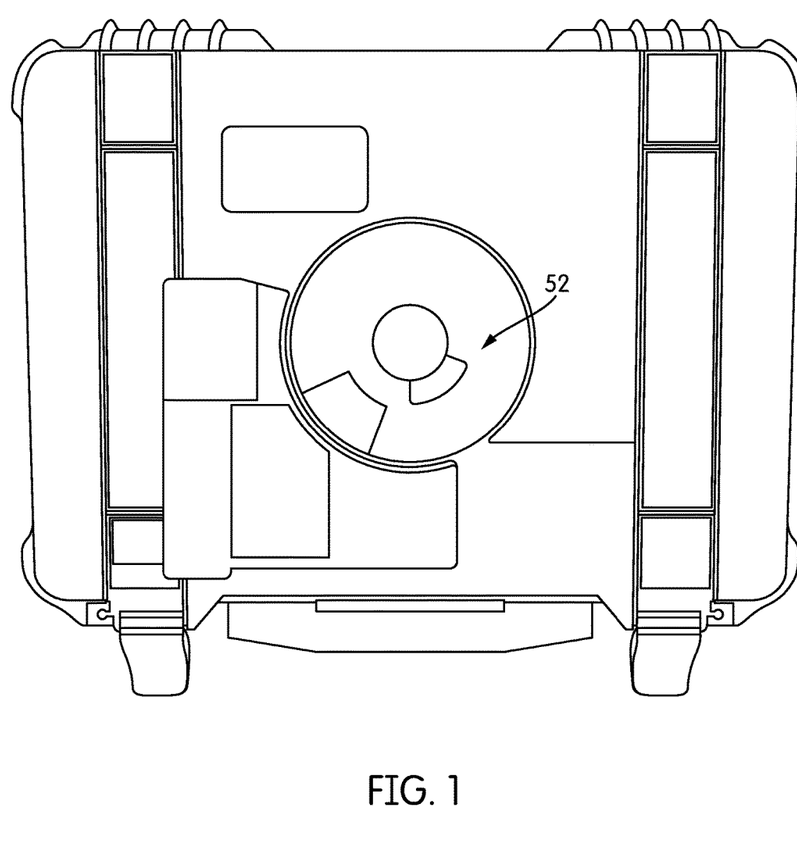
FIG. 1 is an illustration of a package for a portable sterilizer in accordance with an embodiment.

Referring now to FIG. 1, a portable sterilizer may be embodied in a relatively small form factor case 2, for example a sealable case such as are available from Pelican Products of Torrance, Calif. Such cases are generally hard sided and may be made from, for example, polypropylene. A seal may be provided, for example using a polymer o-ring disposed about the opening. Optionally, a purge vent may be included allowing for pressure equalization, for example when the device has been transported by air. The purge vent may include a nonwoven filtering membrane and be sealed with a nitrile o-ring. In an embodiment, the case may be functional in a temperature range from −40 C to 99 C, for example. The case may include additional openings as further described below.

The case is configured to allow for generation of a sterilant gas therein, and is generally gas-tight when closed. It may further include internal structure for supporting items to be sterilized. Such structures may include, without limitation, shelves, slots, or any other suitable support. In an embodiment, items to be sterilized are packaged in pouches that include at least a portion that is permeable to the sterilant gas, but generally impermeable to contaminating particles such as spores or bacteria. Such pouches may incorporate biological or chemical indicators configured to show that the item therein has been appropriately exposed to sterilant gas. The pouches may be made from, for example, Tyvek®, which is generally gas permeable but impermeable to dirt and microbes, or they may incorporate a permeable window and some additional portion that is both impermeable to dirt and microbes and to gases.

The case is further configured to interface with a gas generating module that may be, for example, removably inserted via a port in the case as described below in relation to FIG. 5.

Figure 2:
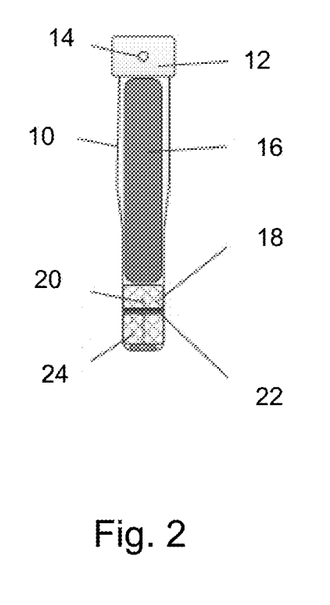
FIG. 2 is a schematic illustration of a gas generation module for use with a portable sterilizer in accordance with an embodiment.

One embodiment of a gas generating module is illustrated in FIG. 2. The gas generating module includes a vial 10, that may be, for example, polycarbonate, though other plastic, glass, or metal materials may be used. A suitable vial size for use with a suitcase sized sterilizer is on the order of a few tens of milliliters. For example, the vial may have a capacity of about 40 ml.

A cap 12 is configured to close the top of the vial 10, and may further include a mechanism for activating the module. Optionally, the cap may include an orifice 14 that provides for gas evacuation upon activation of the module. In an embodiment, the module is shipped and stored with a standard polypropylene or ABS cap which may be removed and replaced with an activator cap when ready for use.

Inside the vial 10 is a frangible ampoule 16 that is configured to contain a sterilant gas precursor material. The frangible ampoule 16 may be, for example, made from glass, borosilicate glass, or 33 expansion glass (a type of borosilicate). Optionally, the glass may include a tint, for example amber or other dark color.

Prior to activation, the ampoule 16 is supported by a spring or a resilient material 18. As an example, the resilient material may include porous foam. The resilient material 18 or spring is configured and arranged to bias the ampoule 16 away from an activation pin 20. When activated, the ampoule 16 is pressed onto the activation pin 20 such that the ampoule is fractured and the sterilant gas precursor material is released into the vial 10 where it is able to contact a second sterilant gas precursor material, which may be, for example, metal foil 22 which reacts with the first precursor to produce the sterilant gas.

In an embodiment, the sterilant gas is NO₂, the metal foil 22 includes copper, and the reaction is:

(I).

That is, aqueous nitric acid reacts with solid copper to form nitrogen dioxide gas as a sterilant along with liquid water and aqueous copper nitrate. Nitrogen dioxide as a sterilant has been described, for example, in U.S. Pat. No. 8,017,074, incorporated by reference herein. Notably, the water produced in the reaction may provide some degree of humidification to the sterilant gas, which may be useful in facilitating sterilization as described in that reference. Particularly, as the reaction is exothermic, the liquid water will tend to evaporate to increase the overall humidity in the chamber.

In an embodiment, adjunct materials may be used to improve the reaction. For example, an emulsifier or anti-foaming agent such as silicon may be included to improve the mixing between the metallic material and the acid. Additionally, neutralizing material 24 such as calcium oxide and/or humidity generating materials may further be included.

Figure 3:
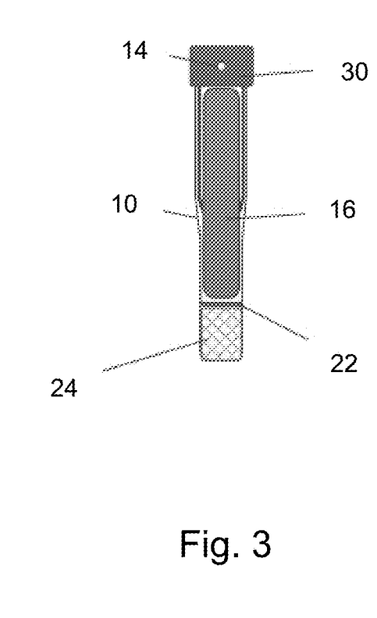
FIG. 3 is a schematic illustration of an alternate gas generation module for use with a portable sterilizer in accordance with an embodiment.

FIG. 3 illustrates an alternate gas generating module that is substantially similar to the module of FIG. 2. It includes the vial 10, and the ampoule 16, just as in the previous embodiment. The cap 30, however, is a cap of the type used in self-contained biological indicator (SCBI) packages such as are available from NAMSA®, of Northwood, Ohio. As in an SCBI, pressing down on the cap causes the ampule 16 to fracture, releasing the sterilant gas precursor material. In this embodiment, the activation pin 20 is omitted. Again, the precursor is permitted to chemically react with a second precursor material such as a metallic foil 22.

In this embodiment, the reaction is the same as given above and the sterilant gas is nitrogen dioxide. In either embodiment, the vial may include a porous filter to prevent or reduce leakage of nitric acid during gas generation. For example, the filter may include a 50 micron polypropylene filter material. Such leakage may result from foaming of the reactants or from the device being placed in a non-level attitude or being moved during the reaction.

The amount of sterilant gas precursor and the amount of material in the second precursor (e.g., the amount of nitric acid and the amount of copper foil) are selected to produce a selected concentration of sterilant gas in the chamber. As will be appreciated, the volume of the chamber may be known in advance such that the selected amount of precursor should give a relatively consistent sterilant concentration within the chamber.

Figure 4:
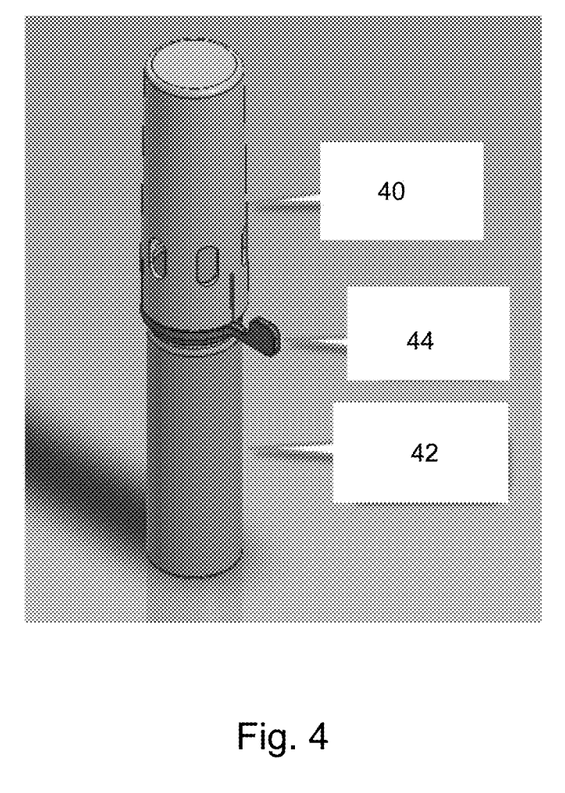
FIG. 4 is a schematic illustration of a gas generation module for use with a portable sterilizer in accordance with an embodiment.

FIG. 4 schematically illustrates an embodiment that may correspond to either of the foregoing embodiments. As shown in FIG. 4, the gas generating module may be embodied in a three part arrangement in which the activator assembly 40 is separated from the nitric acid vial 42 by a safety mechanism 44. The safety mechanism may be, for example, a clip that prevents the activator from pushing down on the glass vial. In this embodiment, prior to insertion into the case, the safety mechanism is removed, allowing activation by whichever of the foregoing methods.

Figure 5:
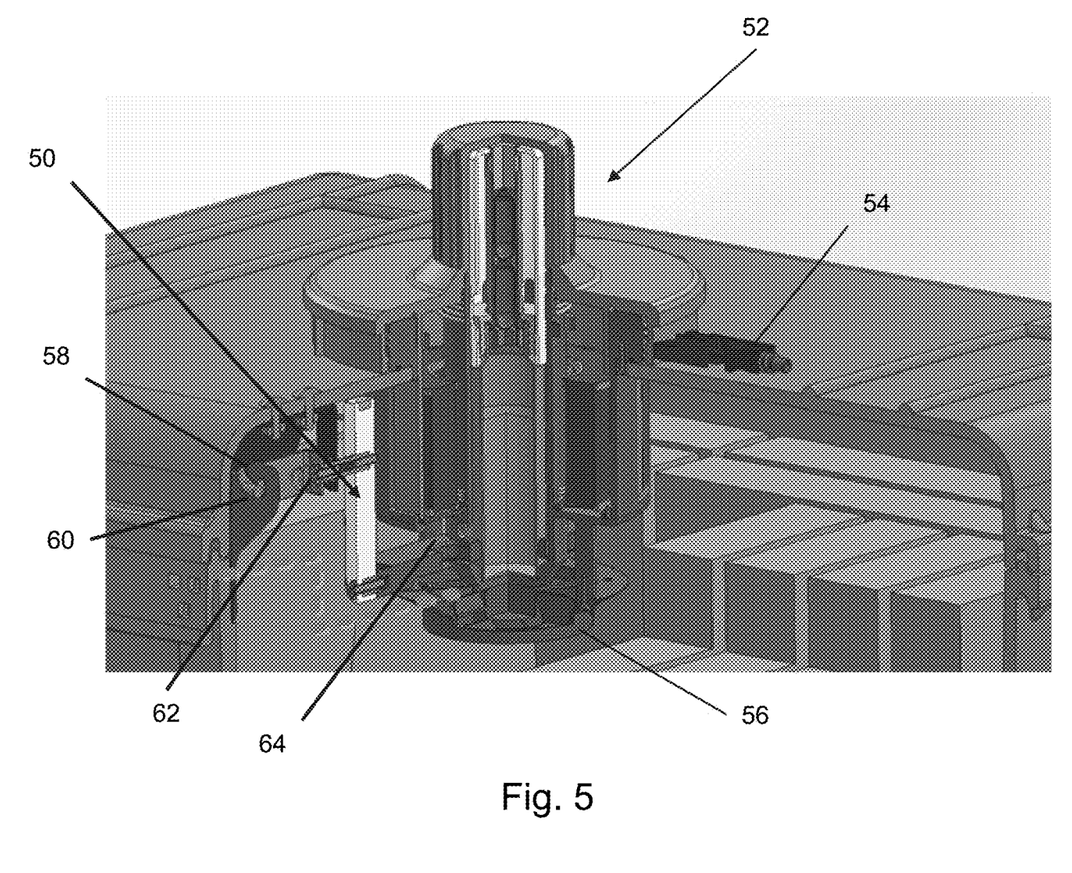
FIG. 5 is schematic illustration of a gas generation module installed in a portable sterilizer in accordance with an embodiment.

FIG. 5 schematically illustrates an interlocking port for use with various embodiments. As illustrated, the gas generating module is inserted into the case, where an interlock latching mechanism 50 prevents activation unless the case is closed. The vial is held in place with a cap 52, which may screw on and may include sealing o-rings about the periphery where it engages the case. A timer switch 54 controls the duration of the sterilizing operation, and is configured to allow sufficient time for the reaction between the precursor materials to fully run. In an embodiment, a sterilization cycle may run for about 8 to 10 hours to ensure sterilization. As will be appreciated, the duration may vary depending on temperature and humidity. A fan 56 may be included to assist in circulating the sterilant gas throughout the case. Notably, in embodiments without such a circulating fan, there is, in principle, no need for any power source to operate the system. That is, the system may be operated in a manner that requires no external energy sources, including electricity, batteries, fuel, or solar. Alternately, a circulating fan incorporating wind-up spring driven power may be used to provide circulation without requiring the use of electrical energy. In an embodiment, battery power may supply low energy functionality and the system may operate independently of any external AC power supply, i.e., without any mains power.

As may be seen in FIG. 5, an embodiment of an interlock includes a hook 58, which is connected to the bottom portion of the case. The hook 58 is configured to engage a pin 60 to oppose a biasing spring 62 that urges a stop 64 into a distal end of the receptacle for the gas generating module. When the pin 60 is engaged with the hook 58 (i.e., when the case 2 is closed), an opening in the stop 64 is positioned such that the gas generating module may be inserted fully into the receptacle. The hook 58 and stop 64 may further be configured such that the case may not be opened as long as the gas generating module is present. As shown in the figure, the stop 64 engages the end of the gas generating module such that it cannot slide when the module is present. As a result, the pin 60 is prevented from disengaging with the hook 58 until the module is removed, allowing free movement of the stop 64.

In operation, the module may be assembled by applying an activator cap of the types described above to the nitric acid vial. The activator cap may be the as-shipped closure, or may alternately be installed by the user just prior to use. In the latter case, an ordinary cap is removed and the activator cap installed in place thereof. If a safety mechanism is included, it is removed and the module is installed in the case. Once installed, the activator cap is operated to allow the precursor materials to interact, producing sterilant gas.

The gas is permitted to remain in circulation within the case for a selected amount of time sufficient to cause sterilization of the items inside. For a concentration of approximately 1%, a dwell time of several hours may be suitable. Biological indicators may be used to ensure that the appropriate level of sterilization has been achieved and chemical indicators may be used to determine that release of the sterilant has occurred.

In an embodiment, a scrubber is included that is configured and arranged to consume the sterilant after the sterilization process is complete. Such a scrubber may include, for example, a medium that chemically binds some or all of the nitrogen dioxide, and converts it into non-reactive products. The scrubber material may be provided in granular form, smaller granules providing a greater surface area per unit volume of scrubbing material.

Figure 6A:
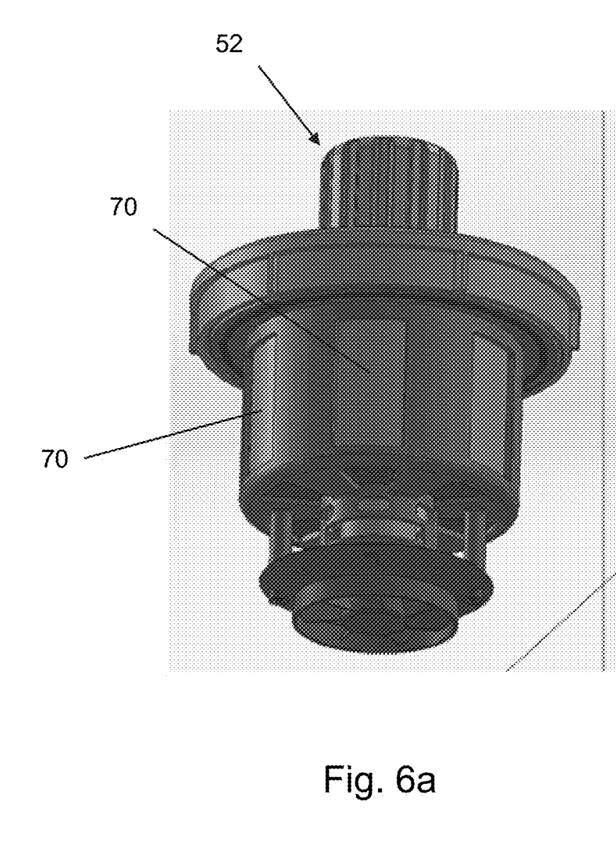
FIGS. 6a and 6b illustrate an embodiment of a shutter controlled sterilant consumption system in accordance with an embodiment.
Figure 6B:
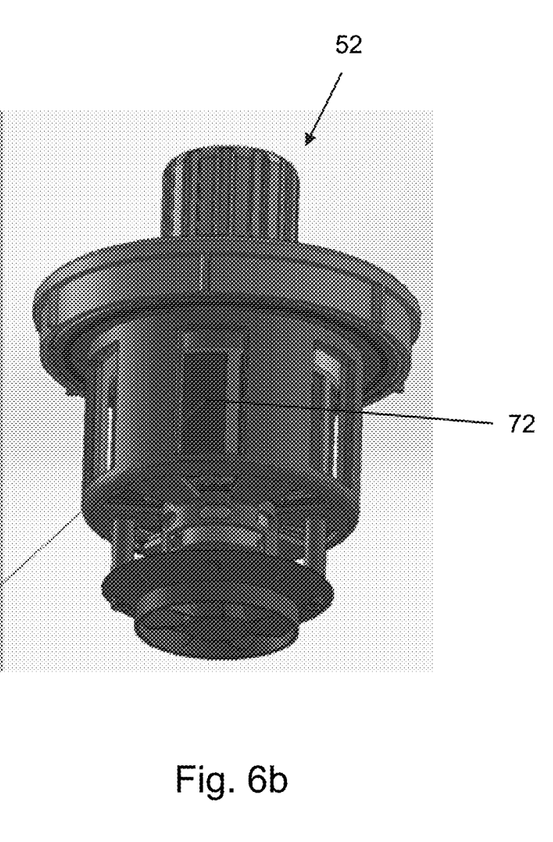

In an embodiment, the cap 52 may be configured to control both the sterilization cycle and the sterilant consumption cycle as illustrated in FIGS. 6a and 6b. In this embodiment, sealing the cap 52 may cause the activator cap to press down, activating the gas generating module. As will be appreciated, this can be achieved either by use of a threaded connection whereby as the cap is rotated or by direct action, it is lowered, thereby initiating gas generation.

During the sterilization cycle, scrubber material is sealed off from the gas by a plurality of shutters 70 as shown in FIG. 6a. For sterilization consumption, the cap is rotated to a second position, wherein the shutters are opened as shown in FIG. 6b, allowing the sterilant gas to interact with the now exposed scrubber material 72, converting it into non-reactive products.

Alternately, an exhaust passage including an inline filter may allow gas to escape to the ambient atmosphere.

In an embodiment, a sodium permanganate material has been found to be suitable for oxidation of NOx to nitrate. In particular, granular Purafil SP (14×28 mesh), a sodium permanganate material including activated alumina has been found to be suitable. Once oxidized, the nitrate bonds with sodium to form a solid salt which is substantially non-toxic, non-corrosive, non-reactive and does not readily ignite. In embodiments, the exhaust gas may be considered to be remediated when $NO_2$ levels are reduced below applicable safety standards, and particularly, when reduced below about 5 ppm and more particularly, when reduced below about 1 ppm. In embodiments where the gas is exhausted directly outdoors, a higher level of $NO_2$ may be acceptable, and levels of 10 ppm may be considered to be sufficiently remediated. A chemical indicator may be employed to provide an indication that the gas within the device has been sufficiently scrubbed.

Figure 7:
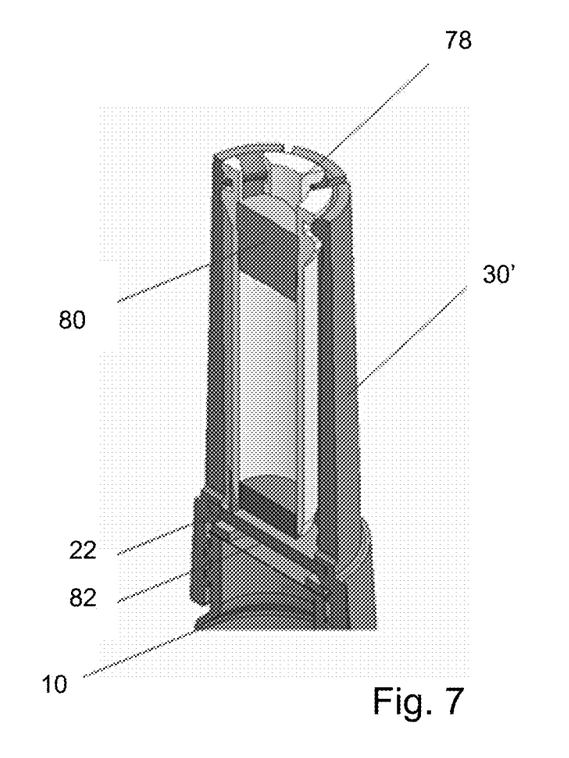
FIG. 7 is a schematic illustration of an alternate embodiment of a gas generation module for use with a portable sterilizer in accordance with an embodiment.

In an alternate embodiment, illustrated in FIG. 7, the gas generating module may include a recessed activating mechanism 78, which may include a porous filter 80. The activating mechanism is held by a stop in snap fit, but sufficient force on the upper surface of the mechanism will push the snap fit past the stop, causing an end of the mechanism to push through a frangible septum 82. When the septum 82 is broken, the metal foil 22 is allowed to drop into the vial and react with its respective gas precursor (e.g., acid) to generate the sterilant gas.

Although the invention has been described in detail for the purpose of illustration based on what are currently considered to be the most practical and preferred embodiments, it is to be understood that such detail is solely for that purpose and that the inventions are not limited to the disclosed embodiments, but, on the contrary, are intended to cover modifications and equivalent arrangements that are within the spirit and scope of the described embodiments. For example, it is to be understood that the present invention contemplates that, to the extent possible, one or more features of any embodiment can be combined with one or more features of any other embodiment. Where the word "about" has been used with respect to numerical ranges, it may generally be understood to mean within a range of ±25%.

What is claimed is:

1. A sterilant gas generating module, comprising:
   a gas-impermeable vial;
   a frangible ampule containing a first sterilant gas precursor material, disposed within the gas-impermeable vial;
   a second sterilant gas precursor material, disposed within the gas-impermeable vial and outside the ampule, the first and second sterilant gas precursor materials being selected to be mutually reactive to generate a sterilant gas; and
   an activation mechanism, configured and arranged to be actuatable to break the frangible ampule to release the first sterilant gas precursor material to allow it to react with the second sterilant gas precursor material to generate the sterilant gas wherein the activation mechanism comprises a movable cap, configured to close an end of the gas-impermeable vial and to be slidably movable with respect to the vial such that when a force is applied to the movable cap the force is transmitted to the frangible ampoule to fracture it.

2. A sterilant gas generating module as in claim 1, wherein:
   the first sterilant gas precursor material comprises an aqueous acid solution and the second sterilant gas precursor material comprises a metallic material.

3. A sterilant gas generating module as in claim 1, wherein the mutual reaction between the first and second sterilant gas generating materials is an exothermic reaction and a reaction product includes water such that the mutual reaction produces water vapor in addition to the sterilant gas.

4. A sterilant gas generating module as in claim 1, wherein the sterilant gas is $NO_2$.

5. A sterilant gas generating module as in claim 1, wherein the activation mechanism comprises:
   a pin, disposed in displaced relation from the ampoule; and
   a resilient member, configured and arranged to bias the ampoule away from the pin, wherein
   such that when the force is applied to the movable cap, the frangible ampoule is pressed against the pin to fracture the ampoule.

6. A sterilant gas generating module as in claim 1, wherein the first sterilant gas precursor material comprises nitric acid and the second sterilant gas precursor material comprises a copper foil.

7. A sterilant gas as in claim 1, further comprising an emulsifier selected to improve mixing between the first and second sterilant gas precursor materials.

8. A sterilant gas generating module, comprising:
   a gas-impermeable vial;
   a container containing a first sterilant gas precursor material, disposed within the gas-impermeable vial;
   a second sterilant gas precursor material, disposed within the gas-impermeable vial and outside the container, the first and second sterilant gas precursor materials being selected to be mutually reactive to generate a sterilant gas; and
   a movable cap, configured and arranged to close an end of the gas-impermeable vial and to be slidably movable with respect to the vial such that when a force is applied to the movable cap, the force is transmitted to create an aperture in the container to allow the first sterilant gas precursor material to react with the second sterilant gas precursor material to generate the sterilant gas.

9. A sterilant gas generating module as in claim 8, wherein the container comprises a septum.

10. A sterilant gas generating module as in claim 9, further comprising a stop, configured to inhibit movement of the movable cap up to a threshold force sufficient to push a snap fit portion of the cap past the stop to allow the force to be transmitted to the septum to create the aperture.

* * * * *